(12) United States Patent
Shi et al.

(10) Patent No.: US 6,783,978 B1
(45) Date of Patent: Aug. 31, 2004

(54) ISOLATION AND CHARACTERIZATION OF THE GENOMIC DNA CLONES OF RIBOSOMAL PROTEIN GENE L25 IN TOBACCO

(75) Inventors: Lifang Shi, Richland, WA (US); Johnway Gao, Richland, WA (US); Brian S. Hooker, Kennewick, WA (US); Ziyu Dai, Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 177 days.

(21) Appl. No.: 09/714,948

(22) Filed: Nov. 20, 2000

Related U.S. Application Data

(60) Provisional application No. 60/167,254, filed on Nov. 19, 1999.

(51) Int. Cl.[7] ...................... C12N 15/00; C12N 15/09; C12N 15/63; C12N 15/70; C12N 158/74
(52) U.S. Cl. .................... 435/320.1; 435/419; 435/468; 536/23.1
(58) Field of Search .................... 536/23.1; 800/298, 800/317.3; 435/320.1, 419, 468

(56) References Cited

FOREIGN PATENT DOCUMENTS

WO    WO 98/21348    5/1998

OTHER PUBLICATIONS

Dai et al. Promoter elements controlling developmental and environmental regulation of a tobacco ribosdomal protein gene L34 XP-002168629 Plant Molecular Biology 32:1055–1065 1996.*

Uemura et al. cloning characterization, and physical location of the fp1Y gene which encodes rebosdomal protein L25 in escherichia coli K12 Mol Glen Genet 1991 226: 341–344.* jeeninga et al. Rat RL23a ribosomal protein efficiencfly competes with its saccharomyces cerevisiae L25 homologue for assembly into 60 S subunits J. Mol. Biol. 1996 263, 648–656.*

R. E. Jeeninga et al., *RAT RL23a Ribosomal Protein Efficiently Competes with its Saccharomyces Cerevisiae L25 Homologue for Assembly into 60 S Subunits*, J. Mol. Biol. vol. 263 No. 5, pp 648–656, 1996.

J. Gao et al., *Developmental and Environmental Regulation of two Ribosomal Protein Genes in Tobbacco, Plant Molecular Biology* vol. 25 No. 5, pp. 761–770, 1994.

J. Gao et al., *Nucleotide and Portein Sequences of 60S Ribosomal Protein L17 from Tobbacco, Database EMBL Sequence Library*, accession No. L18908, 1993.

Z. Dai et al., *Promoter Elements Controlling Developmental and Environmental Regulation of a Tobbacco Ribosomal Protein Gent L34, Plant Molecular Biology*, vol. 32 No. 6, pp. 1055–1065, 1996.

J. Gao et al., *Isolation and Construction of Strong Promoters for the Production of Foreign Proteins in Cultured Plant Cells, American Chemical Society, 205th ACS National Meeting, Abstracts of Paper*, Denver, CO, Mar. 28–Apr. 2, 1993, No. 154.

* cited by examiner

*Primary Examiner*—James Ketter
*Assistant Examiner*—Konstantina Katcheves
(74) *Attorney, Agent, or Firm*—Wells St. John P.S.

(57) ABSTRACT

The promoter of the ribosomal protein gene L25 is operably linked to a structural gene. This chimeric gene is placed in an expression vector. The expression vector containing the chimeric gene is used to transform plants cells and plants. Seeds are obtained from the transformed plants. A product, such as a protein, encoded by the structural gene is isolated from the transformed plant cells and plants.

18 Claims, 6 Drawing Sheets

```
GAATTCTCGA AGATGCCCAT TGTTGAATAA TCGAGCTACT TCTTCCCTTA GCTATAGACA -1015
ATCTTCGGTC CTATGACCCG GAGTACCGTG GTACTTACAC ACCAAGATTG ATCCCTCTAG -955
GCAGGATCAG ACTGCAGTGG TCTAGGCCAC TTGGTCTCTG TCACGACCCG AAAATCCCAC -895
CCTCGGGACC GTGATGGCAC CTAACATTTC ACTTTCTAGG TAAGCCAAAG TTAGAACGGT -835
TTATCCATTT TTAAAAGTTC ACATTAAATA ATAGTAAAGA AACCGAAATA ATTGAAATAA -775
ATTCTGAAGT AAAGTGCGGA AAAACATAAC AATTGAAATA TCTAATACAA CCTCAAATCT -715
GGTGTCACAA GTGCACTAGC TACTAGAATA CTACAAATAA AGGTTTGAAT AAAAGTAAAG -655
TTGTCTGAAA TAAAAATACA CAGCTAAGAT ATAGGAGGAG GGGACTTCAG GGCTGCGAAC -595
GCCGAGCAAT TGTACCTCAA GTCTCCACAC TGATAGTCAA CCCTAGCAAT CTACTGACCG -535
CCGCTAAGAC CGACTCCAAA ATCTTTACAA AAAGTGCAGA GTGTAGTATG AGTACAACCG -475
ACCCCATGTA CTCTGTAAGT ACCGAGCCTA ACCTCGATGA AGTAGTGATG AGGCTAAGGC -415
GGGTCCCTTA CAATATAACC TGTACGTAGT ACAATATAAT GACAGAAACG GAAAATATGG -355
AAACGAAATA AAGAAGCTAA CTCATGAAAA TAAATCAATC TTCGAAGAAA AACTAGTAAA -295
TGCCAGAAAT ACCAATACTA TACCAATCCA CACTTATTTT ACCTGTTGCG GCACGCAACC -235
CAATTCCACC ATATCAATAT AAATTCACCC TTATTTAACA TATCAATCCA CCCTTATTCC -175
ACATGTTGCA CGCAACCCTA TCCCACTATA TCAATATAAA TAAATCAATG TGTGCAAGCA -115
                                      TATA box
ATTTAATAAC TCAAATCAAA AACCCTAATC GGCAGAGCAG CTTCTCTCAA GTAAGATGGT -55 AGATTTCTCG
TAGGGTTTCA TACTGTACCT ATCCAAATGG CTCCAGCTAT CTAGActcag +5 gtaagctggt agatttctcg
tagggtttca tactgtacct atccaaatgg ctccagctaa agGTACACTT CTGAGTCTCT TTTCGGCCAT
TTGATTTCTT TTTTCGGGGA ATAATTTTGT TGTAATTTGA GTTTATTTTA ATAAAACGAT GTGCAGGATA
TGCTTGTTAT GTTGTTGGAA ATGTGAACAG TTGTTGCCTT TTTTTTGTGC TAAAATATAA CTAATTATTG
GGCTTTGCTA CAAAATTTTC TATTCTTTGT GATATTATTA GTGTTGGTTA GATTTCGAA GAAGGTTTTC
AGTATGTTTA TTATTATTTC TGGTAAGGAT ATGAGTACAC TGAAGATTCA TTTATCTGAA CCCAACTTGT
TACTCGTTTG TTATTGTGTA GTAGTAAAGT AGATTCGGTT GTGAGGTTAA TAAATAAGGT AATAACACGA
TGTCGGGTTG AAGTTTGTTA GAACCGCTGC AGTTGTGCTG TTGTAAAAAG GAGTTCAGTT ATTTTGTTGA
GTAGTCTTAT TTCATCTGGT TTTGCTCCTT
TTTATTGAAA TCATTAAAAT ACCAGTCACA GTCATTAGTT TTAGAAACAA CTGGAGGATT ATTAGTTGCA
AAAAGCTTGA TTAATCAGGG GCAGGTTAAT AGGCGGAAGT AGGGCGCCTG TATAAATTTT GGCATTTCAT
GAATTTCTG AAGCTAATAG AATAAGTGCC TTTATTGTTG TCTTTGCAA CTGGAGCATT AACACGCTTC
AGAGTCTTGA AAAATGGGAG AGCAGTTGCG ATGTAGATAG TTTTGCAATT TTGAGAATTT CTTTTTTCTC
TTGAGAGAAA AACACTTTTA TTGGACATAA TTATTATTTT TTGTCCTGTA TAATACAATC AATTATAAAG
CATTAAAATA TTCTAATCAA TTATATAGCG TTCACATATT CTAATTTGGA AGATCATCTA ACATCCTGCT
ACCTAAAGGC TTGAAAATGC AGGAGGTAGA TGTTAGTCTA GGATAAAGAA TTGAGCATTA GAGAGGGAGT
GTGGATAATT GTATGGGTTA TTAAATACTT TTACCATGAG GTAAAAGAGA TTGTTGTTAG TATCTTTGAA
AGTGGATGCT GCTTTTGTTT CTCGCCTTAC AAATAAACTT ATGATATTAA AGCAGCATAT TTTATGCTAG
TTGAAGCTGT TGCTAACTCG AATTTCAAAC TGCACTTGCA Gctgatccgt ccaaaaaatc tgaccccaag
gcacaggcag ctaaggttgc caaggctgtc aagtcaggat caaccttgaa gaaaaagtca caaagataa
ggacaaaagt tacattccac cgacctaaga ctttgaagaa ggatagaaac cccaagtacc ctcgtattag
tgcacctgga aggaacaaac ttgatcagta tgggattcta aagtatcccc tcaccacaga gtctgcaatg
aagaagattg aggacaacaa caccttgtt ttcattgtgg acatcaaggc
tgataaaaag aagattaagg atgccgtgaa gaagatgtat gacattcaga caaagaaagt caataccta
attagGTGAG TTTCCTGCCG TGCTTCTCTT CTTTCCATAG CAAGCCTAAA AAGATAAATT GCAAAGGTAT
ATGTAAGTAT GATTTCATAT GAAAACTGGT TGTCCTCGTG TCAATGATG GCGGAATGTC AGAACTGCAC
AAGGACATTA TATTTCTTTC AGCTGTACGT TTCTGCTTTT ATTCCATATG TATTGCCATG GCGATTCCTT
GCTAAGGTGC TTCCTTGTGT TCCTTTTTCA Ggcctgatgg gacgaagaaa gcatatgtga ggttgactcc
tgactatgat gctttggacg ttgccaacaa aattggaatc atctaaacta gttacctgtc tagaatttta
caagaattta aaatcttgga tttgagttac tagatacact tgaatggaag tgccttgtgt ttttcattct
gaatttgtg tttcagagac aagtttgtt ccgtgtaaaa gatttcactt ttattctcgc attatttatt
tcctgagatt ctctGTCCGA AGATGGAGTA AACTAGTCCT CGTTATTCAT TGTGCTTGCC ATACCACTGT
CATGCCACTT CGAAAATCCT TCCTCGAGAG CCTGTCGCAT CCATGGGTGC CGGCAACATT GAATTGCTTC
TGGAATTGTC AGCCAACTTC TTCTGCGAAG CCTCTGTTCG GGCCAGCATT CAAGCTCTTC
```

```
ACTGCAGTGG TCTAGGCCAC TTGGTCTCTG TCACGACCCG AAAATCCCAC  50
CCTCGGGACC GTGATGGCAC CTAACATTTC ACTTTCTAGG TAAGCCAAAG 100
TTAGAACGGT TTATCCATTT TTAAAAGTTC ACATTAAATA ATAGTAAAGA 150
AACCGAAATA ATTGAAATAA ATTCTGAAGT AAAGTGCGGA AAAACATAAC 200
AATTGAAATA TCTAATACAA CCTCAAATCT GGTGTCACAA GTGCACTAGC 250
TACTAGAATA CTACAAATAA AGGTTGAAT AAAAGTAAAG TTGTCTGAAA 300
TAAAAATACA CAGCTAAGAT ATAGGAGGAG GGGACTTCAG GGCTGCGAAC 350
GCCGAGCAAT TGTACCTCAA GTCTCCACAC TGATAGTCAA CCCTAGCAAT 400
CTACTGACCG CCGCTAAGAC CGACTCCAAA ATCTTTACAA AAAGTGCAGA 450
GTGTAGTATG AGTACAACCG ACCCATGTA CTCTGTAAGT ACCGAGCCTA 500
ACCTCGATGA AGTAGTGATG AGGCTAAGGC GGGTCCCTTA CAATATAACC 550
TGTACGTAGT ACAATATAAT GACAGAAACG GAAAATATGG AAACGAAATA 600
AAGAAGCTAA CTCATGAAAA TAAATCAATC TTCGAAGAAA AACTAGTAAA 650
TGCCAGAAAT ACCAATACTA TACCAATCCA CACTTATTTT ACCTGTTGCG 700
GCACGCAACC CAATTCCACC ATATCAATAT AAATTCACCC TTATTTAACA 750
TATCAATCCA CCCTTATTCC ACATGTTGCA CGCAACCCTA TCCCACTATA 800
TCAATATAAA TAAATCAATG TGTGCAAGCA ATTAATAAC TCAAATCAAA 850
AACCCTAATC GGCAGAGCAG CTTCTCTCAA GTAAG                 885
```

FIG. 3

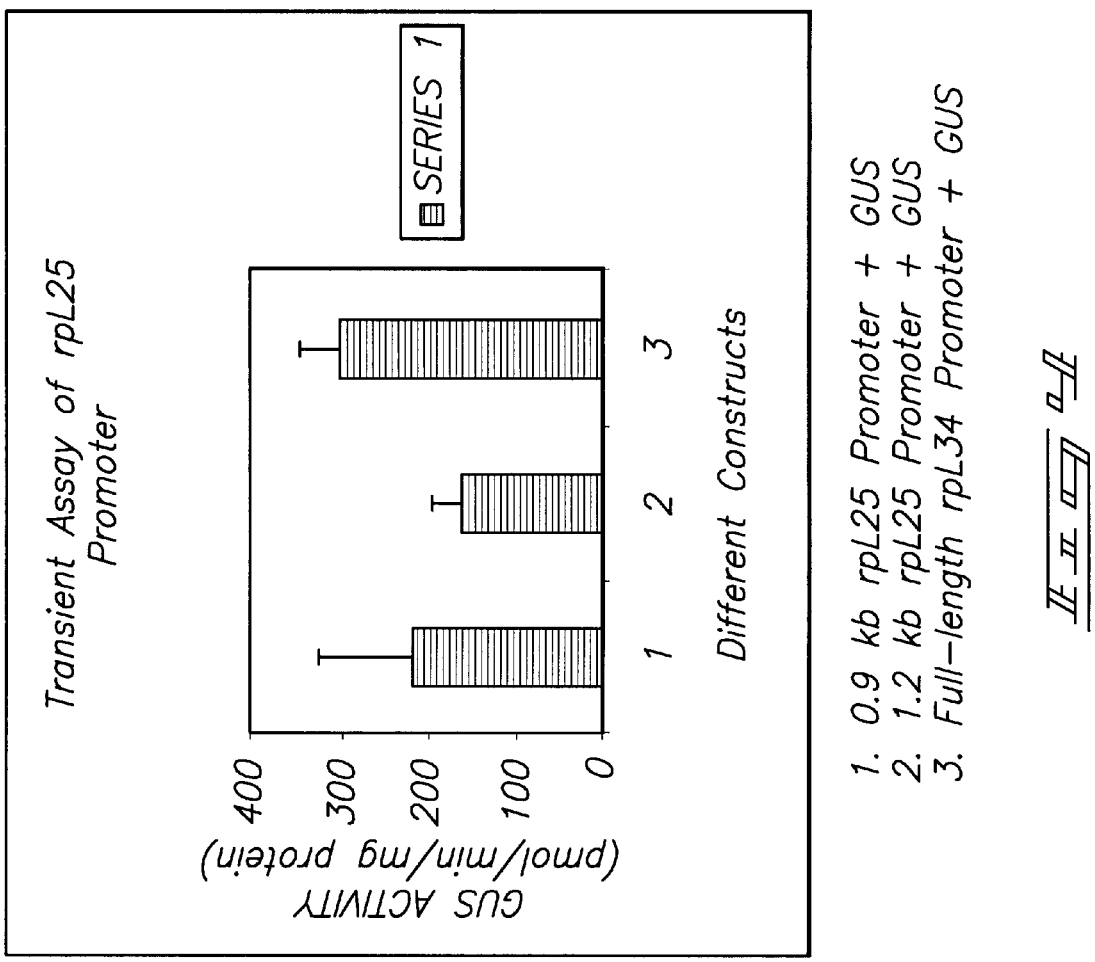

SEQUENCE LISTING

<160> NUMBER OF SEQ ID NOS: 7

<210> SEQ ID NO 1
<211> LENGTH: 3340
<212> TYPE: DNA
<213> ORGANISM: Nicotiana tabacum

<400> SEQUENCE: 1

```
gaattctcga agatgcccat tgttgaataa tcgagctact tcttccctta gctatagaca      60
atcttcggtc ctatgacccg gagtaccgtg gtacttacac accaagattg atccctctag     120
gcaggatcag actgcagtgg tctaggccac ttggtctctg tcacgacccg aaaatcccac     180
cctcgggacc gtgatggcac ctaacatttc actttctagg taagccaaag ttagaacggt     240
ttatccattt ttaaaagttc acattaaata atagtaaaga aaccgaaata attgaaataa     300
attctgaagt aaagtgcgga aaaacataac aattgaaata tctaatacaa cctcaaatct     360
ggtgtcacaa gtgcactagc tactagaata ctacaaataa aggtttgaat aaaagtaaag     420
ttgtctgaaa taaaaataca cagctaagat ataggaggag gggacttcag ggctgcgaac     480
gccgagcaat tgtacctcaa gtctccacac tgatagtcaa ccctagcaat ctactgaccg     540
ccgctaagac cgactccaaa atctttacaa aaagtgcaga gtgtagtatg agtacaaccg     600
accccatgta ctctgtaagt accgagccta acctcgatga agtagtgatg aggctaaggc     660 gggtcccttta caatataacc tgtacgtagt acaatataat gacagaaacg gaaaatatgg     720
aaacgaaata aagaagctaa ctcatgaaaa taaatcaatc ttcgaagaaa aactagtaaa     780
tgccagaaat accaatacta taccaatcca cacttatttt acctgttgcg gcacgcaacc     840
caattccacc atatcaatat aaattcaccc ttatttaaca tatcaatcca cccttattcc     900
acatgttgca cgcaaccta tcccactata tcaatataaa taaatcaatg tgtgcaagca     960
atttaataac tcaaatcaaa aaccctaatc ggcagagcag cttctctcaa gtaagatggt    1020
agatttctcg tagggtttca tactgtacct atccaaatgg ctccagctat ctagactcag    1080
gtaagctggt agatttctcg tagggtttca tactgtacct atccaaatgg ctccagctaa    1140
aggtacactt ctgagtctct tttcggccat ttgatttctt ttttcgggga ataattttgt    1200
tgtaatttga gtttatttta ataaaacgat gtgcaggata tgcttgttat gttgttggaa    1260
atgtgaacag ttgttgcctt ttttttgtgc taaaatataa ctaattattg ggctttgcta    1320
caaaattttc tattctttgt gatattatta gtgttggtta gattttcgaa gaaggttttc    1380
agtatgttta ttattatttc tggtaaggat atgagtacac tgaagattca tttatctgaa    1440
cccaacttgt tactcgtttg ttattgtgta gtagtaaagt agattcggtt gtgaggttaa    1500
taaataaggt aataacacga tgtcgggttg aagtttgtta gaaccgctgc agttgtgctg    1560
```

-continued

```
ttgtaaaaag gagttcagtt attttgttga gtagtcttat ttcatctggt tttgctcctt    1620
tttattgaaa tcattaaaat accagtcaca gtcattagtt ttagaaacaa ctggaggatt    1680
attagttgca aaaagcttga ttaatcaggg gcaggttaat aggcggaagt agggcgcctg    1740
tataaatttt ggcatttcat gaatttcctg aagctaatag aataagtgcc tttattgttg    1800
tctttggcaa ctggagcatt aacacgcttc agagtcttga aaaatgggag agcagttgcg    1860
atgtagatag ttttgcaatt ttgagaattt cttttttctc ttgagagaaa aacactttta    1920
ttggacataa ttattatttt ttgtcctgta taatacaatc aattataaag cattaaaata    1980
ttctaatcaa ttatatagcg ttcacatatt ctaatttgga agatcatcta acatcctgct    2040
acctaaaggc ttgaaaatgc aggaggtaga tgttagtcta ggataaagaa ttgagcatta    2100
gagagggagt gtggataatt gtatgggtta ttaaatactt ttaccatgag gtaaaagaga    2160
ttgttgttag tatctttgaa agtggatgct gcttttgttt ctcgccttac aaataaactt    2220
atgatattaa agcagcatat tttatgctag ttgaagctgt tgctaactcg aatttcaaac    2280
tgcacttgca gctgatccgt ccaaaaaatc tgaccccaag gcacaggcag ctaaggttgc    2340
caaggctgtc aagtcaggat caaccttgaa gaaaaagtca caaagataaa ggacaaaagt    2400
tacattccac cgacctaaga ctttgaagaa ggatagaaac cccaagtacc ctcgtattag    2460
tgcacctgga aggaacaaac ttgatcagta tgggattcta aagtatcccc tcaccacaga    2520
gtctgcaatg aagaagattg aggacaacaa caccccttgtt ttcattgtgg acatcaaggc    2580
tgataaaaag aagattaagg atgccgtgaa gaagatgtat gacattcaga caaagaaagt    2640 caataccta attaggtgag tttcctgccg tgcttctctt ctttccatag caagcctaaa    2700
aagataaatt gcaaaggtat atgtaagtat gatttcatat gaaaactggt tgtcctcgtg    2760
tcaattgatg gcggaatgtc agaactgcac aaggacatta tatttctttc agctgtacgt    2820
ttctgctttt attccatatg tattgccatg gcgattcctt gctaaggtgc ttccttgtgt    2880 tccttttttca ggcctgatgg gacgaagaaa gcatatgtga ggttgactcc tgactatgat    2940
gctttggacg ttgccaacaa aattggaatc atctaaacta gttacctgtc tagaatttta    3000
caagaattta aaatcttgga tttgagttac tagatacact tgaatggaag tgccttgtgt    3060
ttttcattct gaattttgtg tttcagagac aagttttgtt ccgtgtaaaa gatttcactt    3120
ttattctcgc attatttatt tcctgagatt ctctgtccga agatggagta aactagtcct    3180
cgttattcat tgtgcttgcc ataccactgt catgccactt cgaaaatcct tcctcgagag    3240
cctgtcgcat ccatgggtgc cggcaacatt gaattgcttc tggaattgtc agccaacttc    3300
ttctgcgaag cctctgttcg ggccagcatt caagctcttc                          3340
```

<210> SEQ ID NO 2
<211> LENGTH: 885
<212> TYPE: DNA
<213> ORGANISM: Nicotiana tabacum

<400> SEQUENCE: 2

```
actgcagtgg tctaggccac ttggtctctg tcacgacccg aaaatcccac cctcgggacc      60
gtgatggcac ctaacatttc actttctagg taagccaaag ttagaacggt ttatccatt     120 ttaaaagttc acattaaata atagtaaaga aaccgaaata attgaaataa attctgaagt    180
aaagtgcgga aaaacataac aattgaaata tctaatacaa cctcaaatct ggtgtcacaa    240
gtgcactagc tactagaata ctacaaataa aggtttgaat aaaagtaaag ttgtctgaaa    300
taaaaataca cagctaagat ataggaggag gggacttcag ggctgcgaac gccgagcaat    360
```

-continued

```
tgtacctcaa gtctccacac tgatagtcaa ccctagcaat ctactgaccg ccgctaagac    420
cgactccaaa atctttacaa aaagtgcaga gtgtagtatg agtacaaccg accccatgta    480
ctctgtaagt accgagccta acctcgatga agtagtgatg aggctaaggc gggtcccttk    540
caatataacc tgtacgtagt acaatataat gacagaaacg gaaatatgg aaacgaaata     600 aagaagctaa ctcatgaaaa taaatcaatc ttcgaagaaa aactagtaaa tgccagaaat    660
accaatacta taccaatcca cacttatttt acctgttgcg gcacgcaacc caattccacc    720
atatcaatat aaattcaccc ttatttaaca tatcaatcca cccttattcc acatgttgca    780 cgcaaccota tcccactata tcaatataaa taaatcaatg tgtgcaagca atttaataac    840
tcaaatcaaa aaccctaatc ggcagagcag cttctctcaa gtaag                    885
```

<210> SEQ ID NO 3
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 3
ctcaggtaag ctggtagatt tctcgt                                          26

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 4
tacacggaac aaaacttgtc tctga                                           25

<210> SEQ ID NO 5
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 5
gtgaggttga ctcctgacta tgatgctttg ga                                   32

<210> SEQ ID NO 6
<211> LENGTH: 42
<212> TYPE: DNA
<213> ORGANISM: Artificial Sequence
<220> FEATURE:
<223> OTHER INFORMATION: Description of Artificial Sequence: Primer

<400> SEQUENCE: 6
gtctagatag ctggagccat ttggataggt acagtatgaa ac                        42

<210> SEQ ID NO 7
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucletide

```
<400> SEQUENCE: 7
gtctagattg gataggtaca gtatgaaacc ct                              32
```

ISOLATION AND CHARACTERIZATION OF THE GENOMIC DNA CLONES OF RIBOSOMAL PROTEIN GENE L25 IN TOBACCO

This application is based on provisional application No. 60/167,254, filed Nov. 19, 1999.

BACKGROUND OF THE INVENTION

1. Field of the Invention

The present invention is broadly concerned with the promoter of the ribosomal protein gene L25. More particularly, the present invention relates to an isolated DNA molecule and an expression vector, each of which comprises the promoter of the ribosomal protein gene L25; a plant cell and a plant, each of which is transformed with this expression vector; a seed obtained from this plant; and a method for producing a product from this plant or plant cell.

2. Description of the Related Art

As components of ribosomes, ribosomal proteins (r-proteins) are critical in protein biosynthesis required for cell division and cell differentiation. Studying the expression of ribosomal protein genes and their regulation enables one to differentiate the functions of important housekeeping genes in plant growth and development. Moreover, some promoters of ribosomal protein genes, due to their high expression and complex regulation patterns, are among the most suitable candidates for expressing exogenous genes that are of economic or medical importance.

Different plant ribosomal protein genes appear to have different expression patterns that are regulated in a complicated fashion, a conclusion drawn from studying at least 12 small (S) ribosomal genes and 13 large (L) ribosomal genes from a variety of tissues in several plants (Lee et al. 1999. Gene 226:155–163). Among these 25 ribosome protein genes, L3 and L16 in Arabidopsis (Kim et al. 1990. Gene 93:177–182; Williams et al. 1995. Plant J. 8:65–76) and S15a in rapeseed (Bonham-Smith et al. 1992. Plant Mol. Biol. 18:909–919) were highly expressed in all rapidly proliferating organs, including shoot and root apical meristems, lateral root primordial and early developing stages of reproductive organs. This pattern of ribosomal protein gene expression is consistent with that of most ribosomal protein genes in prokaryotes (Mager 1988. Biochim Biophys. Acta 949:1–15). The rpL16 in Arabidopisis is encoded by two genes (rpLA and rpL16B), and both are mainly regulated in the level of transcription (Williams et al. 1995. Plant J. 8:65–76), ribosomal protein genes in prokaryotes (Mager 1988. Biochim Biophys. Acta 949:1–15). The rpL16 in Arabidopisis is encoded by two genes (rpLA and rpL16B), and both are mainly regulated in the level of transcription (Williams et al. 1995. Plant J. 8:65–76), similar to the plastid ribosomal protein L21 (RPL21) in spinach (Lagrange et al. 1997. Plant Cell 9:1469–1479). While RPL 16A was mainly found in proliferating tissues including the shoot and root apical meristems and auxin-induced lateral root primordia, RPL 16B was highly expressed in cells in the root stele, anthers, and auxin-induced lateral root primordia.

The expression of S19 and L7 in potato increased at the transcription level in the stolon tip during the early stages of tuberization but maintained at a low level in leaves, stems, and roots throughout the development (Taylor et al. 1992. Plant Physiol. 100:1171–1176). Genes S11and S13 in maize were expressed at higher transcriptional level in roots and shoots of developing seedlings than in fully expanded leaf tissues (Lebrun et al. 1991. Plant Mol. Biol. 17:265–268; Joanin et al. 1993. Plant Mol. Biol. 21:701–704). The levels of L27 mRNA in pea were increased remarkably by decapitation, a treatment that leads to cell proliferation (Stafstrom et al. 1992. Plant Physiol. 100:1494–1502; Stafstrom et al. 1995. Plant Mol. Biol. 29:255–265). The transcript of S16 in rice was essentially the same across different tissues and development stages (Zhao et al. 1995. Plant Physiol. 107:1471–1472)

The further understanding of the mechanism of how genes are regulated at transcription level can be greatly enhanced by identifying cis-acting elements, their binding protein(s) and their interaction. By transient and stable transfection analysis of RPL21 promoter deletion mutants, Lagrange et al. (1997) identified a strong core promoter sufficient to drive high levels of gene expression and two non-overlapping positive and negative domains that modulate core promoter activity independently of light. Further, gel retardation analysis showed that a cis-acting element located in the positive domain (S2) binds a leaf-specific nuclear factor (S2F). The rpL34 promoter region recently has been characterized and two synergically functional, yet separable cis-acting elements, have been defined (Shi et al. 1999. Amer. Soc. Plant Physiol. Annual Meeting, Baltimore, Md.).

In a previous study, one cDNA encoding tobacco ribosomal protein L25 (rpL25), which RNA is most abundant in three-day-old cell suspension culture and post germinating seedlings, was isolated and partially characterized. L25 mRNA levels increased in response to wounding and plant hormone treatment (Gao et al. 1993. American Chemical Society Symposium in Denver), a pattern similar to the expression of L27 gene. In this investigation, rpL25 genomic DNA clones were isolated and partially characterized. A preliminary functional analysis of the promoter was performed to gain insights of the expression of rpL25 gene.

SUMMARY OF THE INVENTION

The present invention is directed to an isolated DNA molecule comprising the promoter of the ribosomal protein gene L25, wherein the promoter is preferably the promoter of *Nicotiana tabacum*, and the promoter ideally comprises the nucleotide sequence shown in FIG. 3.

The invention also concerns an expression vector comprising the promoter of the ribosomal protein gene L25 and a structural gene operably linked thereto, wherein the promoter is preferably the promoter of *Nicotiana tabacum*, and the promoter ideally comprises the nucleotide sequence shown in FIG. 3.

Additionally, the invention relates to a plant cell or whole plant transformed with one of the above-described expression vectors, and to seed obtained from one of these plants.

Finally, the invention is directed to a method for producing a product, e.g., a protein, from one of the above-described plants or plant cells, comprising providing the plant or plant cell, causing a product encoded by the structural gene to be produced in the plant or plant cell, and isolating the product from the plant or plant cell, thereby producing the product.

BRIEF DESCRIPTION OF THE DRAWINGS

FIG. 2 shows the sequence of the rpL25 gene. The DNA sequence (SEQ ID NO: 1) of the rpL25 gene is shown. The 5' end of the rpL25 transcripts maps to nucleotide +1. The introns and 5' and 3' untranscribed regions were represented as upper case letters while the transcribed regions were presented bolded lower case letter. The putative TATA box is underlined.

FIG. 3 shows the nucleotide sequence of a DNA fragment (SEQ ID NO: 2) of the rpL25 gene having promoter activity.

FIG. 4 shows the results of the transient analysis of the rpL25 promoter. The GUS activity (pmol/min/mg protein) was averaged from at least three independent experiments ± standard deviation. Lanes 1, 2 and 3 represent the activity from constructs rpL25-2GUS, rpL25-3GUS, rpL34-GUS, respectively.

Other objects, features, and advantages of the present invention will become apparent from the following detailed description. It should be understood, however, that the description and the specific examples, while indicating preferred embodiments of the invention, are given by way of illustration only, because various changes and modifications within the spirit and scope of the invention will become apparent to those skilled in the art from this detailed description.

DETAILED DESCRIPTION OF THE PREFERRED EMBODIMENT

EXAMPLE 1

This example describes the steps for isolating and sequencing of the rpL25 gene.

1.1 Isolation and Sequencing of rpL25 Coding Region

DNA manipulations were conducted using standard procedures as described by Sambrook et al. 1989. *Molecular Cloning: A Laboratory Manual,* 2nd Edition, Cold Spring Harbor Press, Cold Spring Harbor, N.Y. Tobacco genomic DNA was isolated from young leaves of *N. tabacum* Xanthi according to standard methods (Chomczynski et al. 1987. *Anal Biochem.* 162:156–159). About 2 μg of genomic DNA was used as a DNA template to amplify the coding region of the rpL25 gene by PCR, using specific 5' (5'-CTCAGGTAAGCTGGTAGATTTCTCGT-3' (SEQ ID NO: 3) from position +1 to +26) and 3' primers (5'-TACACGGAACAAAACTTGTCTCTGA-3' (SEQ ID NO: 4) from position +623 to +647). Subsequently, the PCR product was subcloned into EcoRV digested pBluescript SK (−). This clone was sequenced using a primer walking strategy, starting with an oligonucleotide located beyond the polylinker cloning site. Sequence data were compiled and analyzed using Bestfit program sequence analysis package (Genetics Computer Group, Madison, Wis.) with adjustments made by inspection when appropriate.

1.2 Sequence and Structure of rpL25 Coding Region

Figure 1:
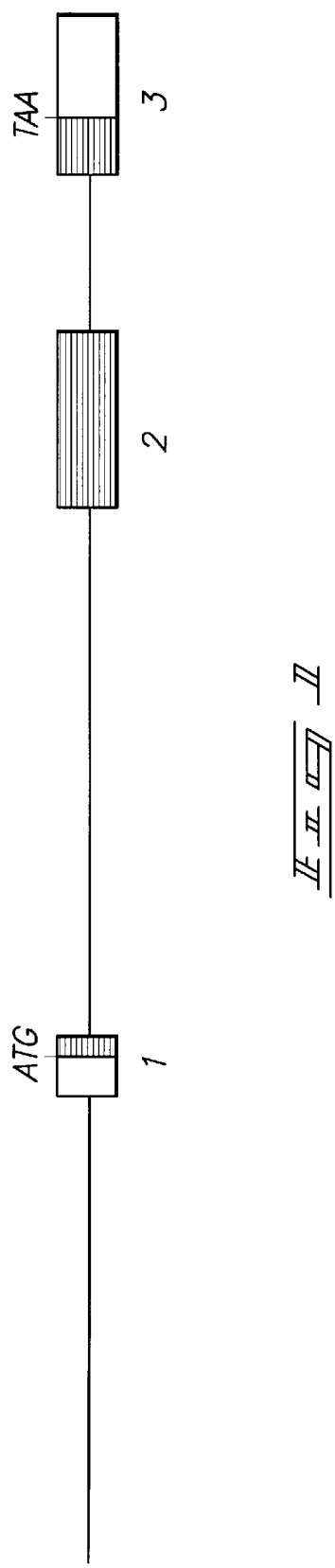
FIG. 1 illustrates the structure of the tobacco rpL25 gene. Exons are represented by numbered boxes. Introns and 5' and 3' nontranscribed regions are represented by lines. The open (white) regions of exon 1 and 3 correspond to untranslated sequences. ATG and TAA represent putative translation start and stop codons, respectively.

Total genomic DNA was used as a template in PCR to amplify the entire rpL25 coding region including its exons and introns by using two primers corresponding to the very 5' and 3' end of rpL25 cDNA. A 2.1-kb PCR product (rpL25-1) was subcloned and completely sequenced. The comparison between the sequence of rpL25 cDNA and rpL25-1 reveals that rpL25-1 contains the whole rpL25 cDNA with two exceptions: the last 47 nucleotides at 3'-end of cDNA are located outside the 3' primer and the rpL25 gene has two introns and three exons. Intron 1 and 2 are 1149 bp and 236 bp long, respectively. Exons 1, 2 and 3 are 67 bp, 364 bp and 263 bp long, respectively (FIG. 1). As shown in FIG. 2, the sequence of three exons was perfectly matched with that of cDNA as reported by Gao et al. (1993. American Chemical Society Symposium in Denver) and two predicted introns have the 5'-GT-AG-3' consensus intron boundary sequences (Shapiro et al. 1987. Nucleic Acids Res. 15:7155–7174).

EXAMPLE 2

This example describes the steps taken to isolate the promoter region of the rpL25 gene.

2.1 Isolation of the rpL25 Promoter Region by PCR

Two PCR-based approaches were taken to isolate the rpL25 promoter region. One was standard inverse PCR in which total tobacco genomic DNA was used as a template. The 5' primer is 5'-GTGAGGTTGACTCCTGACTATGATGCTTTGGA-3' (SEQ ID NO: 5)(corresponding to position +1 to +26 at 3' end of cDNA), while the 3' primer is 5'-GTCTAGATAGCTGGAGCCATTTGGATAGGTACA GTATGAAAC-3' (SEQ ID NO: 6)(corresponding to position +30 to +65 relative to the transcriptional start site and containing a Xbal site at 5' end). The total genomic DNA was digested with EcoRI and self-ligated by T4 ligase. The second PCR analysis was performed by using the phage DNA isolated from tobacco genomic library (Xanthi-nc in EMBL3 clone vector, Clonetech) as a template. The 5' primer was designed based on the adjacent vector region of the genomic DNA fragment cloning site, while the 3' primer was based on the very 5' end of rpL25 cDNA (5'-GTCTAGATAGCTGGAGCCATTTGGATAGGTACAG TATGAAAC-3') (SEQ ID NO: 6) from position +30 to +65 relative to the transcriptional start site) and containing a Xbal restriction site at 5' end. Phage DNA was prepared by extraction of phenol and phenol: chloroform (1:1 v/v), following 5 min of heat at 100° C. Two products, rpL25-2 from the standard inverse PCR and rpL25-3 from genomic library-based PCR, were subcloned and sequenced as described earlier.

2.2 Sequencing Analysis of the rpL25 Promoter

Two PCR fragments were produced, a 1.2-kb DNA fragment (rpL25-2) from total genomic DNA based PCR and a 0.9-kb fragment (rpL25-3) from genomic DNA library based PCR, respectively. Comparison of their sequences indicates that rpL25-3 is completely contained in rpL25-2. The 5' ends of the promoter regions of rpL25-2 and rpL25-3 are located in the region of −1075 and −942, respectively (FIG. 2). Only the sequence of rpL25-2 was shown in FIG. 2. The putative TATA box (TATAAAT) is present at position −140 and −134 upstream of the putative transcriptional start site.

EXAMPLE 3

This example describes the materials and strategies used for gene cloning, protoplast transient assays and stable transformation assays of the expression of a reporter gene under the control of the tobacco rpL25 promoter. This system can be used to study the function of promoter fragments by evaluating the transcriptional activity of its driven reporter gene.

3.1 Bacterium Strain and Plant Materials

*Escherichia coli* DH5α ( was used as the host for routine cloning experiments. The *A. tumefaciens* strain PC2760 was the host for the binary vectors. *N. tabacum* cell suspension culture designated NT1 was used for electroporation experiments. *N. tabacum* cv SR1 and Xanthi-nc were used as the hosts for Agrobacterium-mediated transformation and for genomic DNA isolation, respectively.

3.2 Construction of rpL25 Promoter/GUS Fusion Genes

To prepare the transcriptional fusion construct rpL25-3GUS, the 0.9-kb rpL25-3 was amplified by PCR using rpL25-3 as a DNA template and placed a XbaI restriction site one nucleotide upstream of the putative translation start site. An oligonucleotide (5'-GTCTAGATTGGATAGGTACAGTATGAAACCCT-3') (SEQ ID NO: 7) complementary to the 5' untranslated region of the rpL25 gene and containing XbaI site at 5' end was synthesized and used a 3' primer. The oligonucleotide complementary to the adjacent vector region of the genomic cloning described earlier served as the opposing primer in PCR. The amplified 0.9-kb PCR product was subcloned into EcoRV digested pBluescript SK (-), excised by restriction enzymes digestion of PstI (from the cloning vector) and XbaI (newly introduced at one nucleotide upstream of the putative translation start site), and inserted into the same sites of pBI221, producing rpL25-3GUS. Similarly, rpL25-2GUS was prepared except that the primer (5'-TACACGGAACAAAACTTGTCTCTGA-3'(SEQ ID NO: 4) from position +623 to +647) described earlier served as the opposing primer, where rpL25-2 was used as the DNA template. The XbaI/EcoRI (filled-in) 1.2-kb amplified PCR product was inserted into the XbaI/HindIII (blunt end) sites of pBI221, producing rpL25-2GUS. Both rpL25-2GUS and rpL25-3GUS were used for transient assays. Further, the HindIII/SacI rpL25-3 promoter/GUS reporter gene fragment in rpL25-3GUS was cloned as a cassette into the same sites of the plant expression vector pGA482 (An et al. 1 987. Meth. Enzymol. 153:293–305), producing rpL25-3BGUS for stable transformation in tobacco.

3.3 Transient and Stable Transformation Assays in Tobacco

Electroporation of tobacco protoplasts was performed as described in Ebert et al. (1987. Proc. Natl. Acad. Sci. USA 84:5745–5749) with a slight modification. Test DNA (20 µg) and carrier DNA (10 µg) were used in each electroporation. Protoplasts were incubated in the dark at 29° C. for 48 h before they were collected for protein extraction and MUG assays. The HindIII/SacI promoter-GUS reporter fragments in pBI221 were inserted into the plant expression vector pGA482. Transfer of these constructs into *A. tumefaciens* strain CP2670 was conducted using the freeze-and-thaw method as described by Ebert et al. (1987. Proc. Natl. Acad. Sci. USA 84:5745–5749). Plasmid DNA from the transformed Agrobacterium clones was isolated and digested with various specific restriction enzymes and analyzed in agarose gel to confirm transformation of each construct. Tobacco leaf disc transformation and plant regeneration were performed as described by An et al. (1987. Meth. Enzymol. 153:293–305). At least 30 independent transformants were regenerated. $T_1$ seeds were collected and grown under sterile conditions on agar media containing MS medium (Murashige et al. 1962. Physiol. Plant 15:473–497) with 50 µg ml$^{-1}$ kanamycin and 250 µg ml$^{-1}$ cefotaxin. Kanamycin resistant $T_1$ seedlings were selected, transferred to soil and grown to maturity.

3.4 Fluorometric and Histochemical Analysis of GUS Activity

To prepare for histochemical staining, regenerated plants were allowed to self pollination and surface sterilized $T_1$ seeds were germinated on MS medium containing 50 µg/ml kanamycin and 250 µg/ml cefetaxin. Plants at different development stages, seeds and longitudinally excised flowers were collected and histochemically analyzed as described by Dai et al. (1996. Plant Mol. Biol. 32:1055–1065).

Fluorometric quantitation of GUS activity was performed according to Jefferson et al. (1987. EMBO J. 6:3901–3907). Fresh post germinating seeds and whole seedlings from independent transgenic tobacco were ground in lysis buffer (50 mM sodium phosphate, pH 7.0, 10 mM EDTA, 0.1% TritonX- 100, 0.1% sarkosyl and 10 mM DTT). Tobacco protoplast protein was extracted in the same buffer by 2× sonication on ice or 5 seconds. Protein concentrations were determined by the Bio-Rad method (Bradford 1976. Anal. Biochem. 72:248–254). Approximately 5–10 µg of protein was incubated in the presence of 1 mM 4-methylumbelliferyl β-D-glucuronide in 100 µl of lysis buffer at 37 C. Samples were taken at 0, 15, and 30 min and the enzymatic reaction was quenched in 0.2 M sodium carbonate ($Na_2CO_3$). The fluorometer was calibrated with 100, 200, 300, and 400 nM 4-methylumbelliferon in 0.2M sodium carbonate.

3.5 Transient Analysis of GUS-fused rpL25 Promoter

To evaluate rpL25 promoter expression in tobacco suspension culture, two transcriptional GUS reporter gene fusion constructs (rpL25-2GUS and rpL25-3GUS) were prepared by PCR, subcloned into the pBI221 vector and delivered into tobacco protoplasts by electroporation. MUG assays of protein extracted from tobacco protoplasts showed that high GUS activity was found in tobacco protoplasts containing either promoter (FIG. 4). The activity is about half of the promoter of rpL34, a strongly expressed tobacco ribosomal protein gene studied in our laboratory (Shi et al. 1999). While GUS activity was higher in the construct containing 0.9-kb rpL25-3 than 1.2-kb rpL25-2, the difference did not reach a significant level. These results suggest that the DNA fragment in the region of −1075 to −942 probably plays no role in promoter function.

3.6 Stable Transformation Analysis of rpL25-2BGUS

Figure 5:
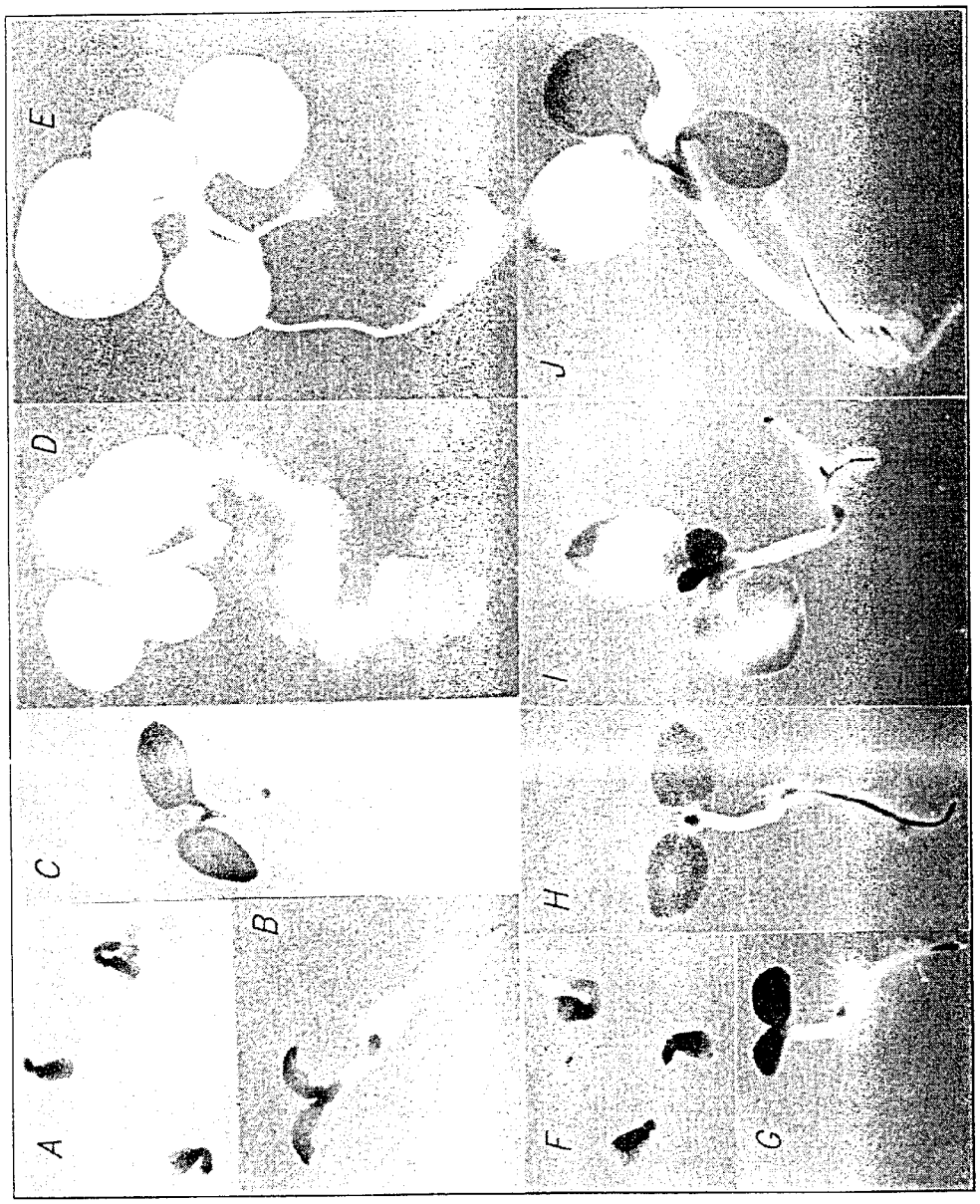
FIG. 5 illustrates histochemical staining of transgenic tobacco. Panels A to E are from transgenic plants containing the rpL25 promoter; Panels F to J are from transgenic plants containing rp134 promoter. The plant materials are from 3-day post-germinating seeds (Panels A and F), seedlings at days 6 (Panels B and G), 9 (Panels C and H), 12 (Panels D and I), and 16 (Panels E and J) post germination.
Figure 11:
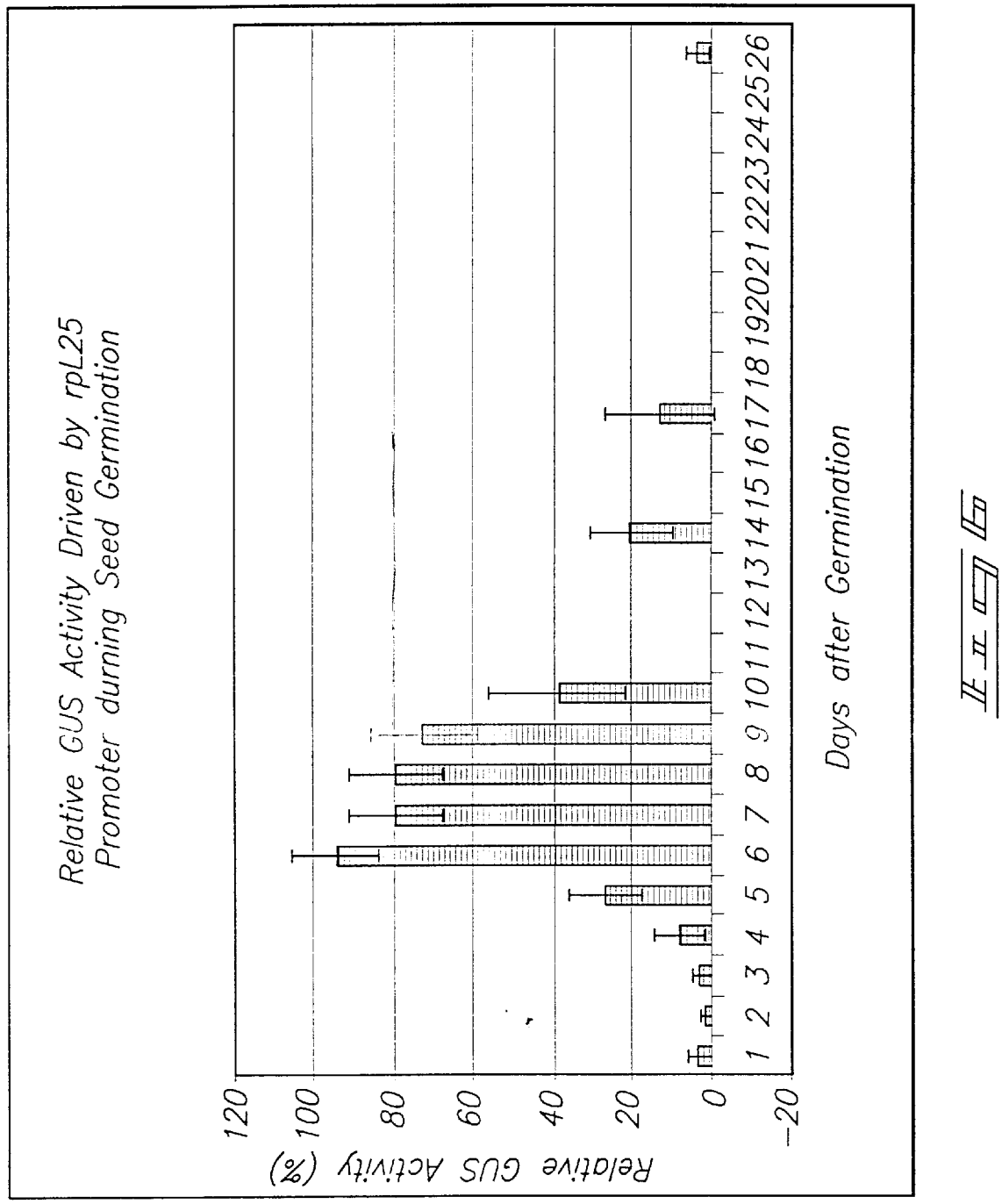
Figure 6:
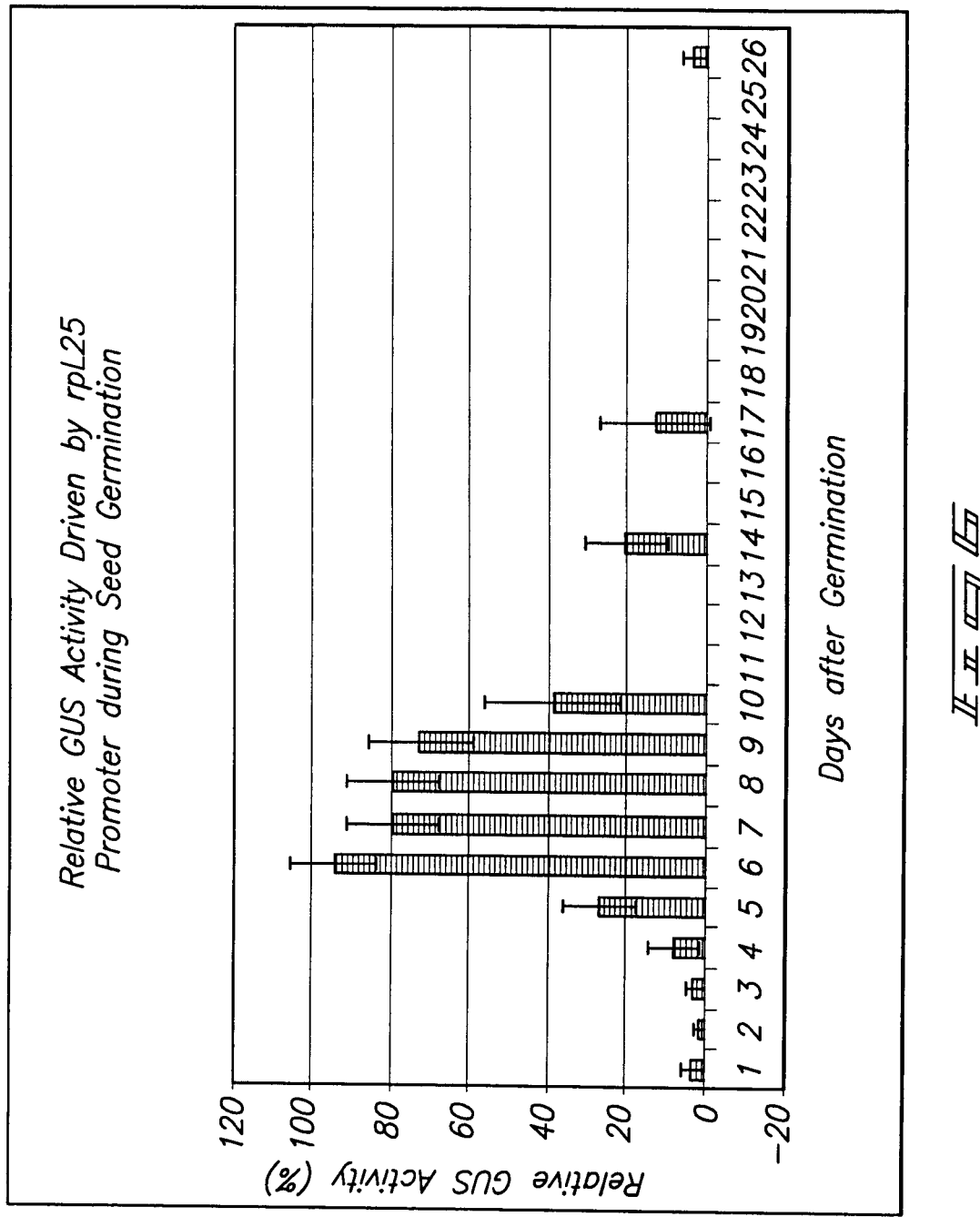
FIG. 6 illustrates relative GUS activity driven by the rpL25 promoter during/post seed germination. GUS activity of seedlings from seven transgenic plants was measured at various time intervals post-germination. The highest measured GUS activity was assigned a value of 100. The remaining GUS activities during/post seed germination are normalized to this value. The vertical bars show the standard deviation.

The 0.9-kb rpL25-3 promoter fragment was studied further, due to its higher activity in transient assays, to investigate spatial regulation of the rpL25 promoter. The transcriptional fusion construct (rpL25-2BGUS) was prepared by inserting the rpL25-3 promoter/GUS reporter gene fragment as a cassette into a plant expression binary vector. The chimeric promoter-GUS construct was transferred into tobacco via Agrobacterium. At least 15 independent transformants were regenerated and allowed to self-pollination. No GUS staining was detected in primary transformants with a low level of GUS activity detected in very young leaves. Our research emphasis was activities seen during seed germination and in younger seedlings. $T_1$ seeds were germinated and the seedlings at different growth stages were harvested for both GUS activity measurement and histochemical analysis. The results of histochemical analysis are shown in FIG. 5. In comparison with transgenic plants containing rpL34 promoter, in which GUS staining was observed in the root meristemic region (Panels F–J, FIG. 5), GUS activity in roots regulated by the rpL25 promoter was undetectable using both GUS staining and histochemical analysis (Panels A–E, FIG. 5). As for tissues with detectable GUS staining, high variation in GUS activity across different transformants was found (data not shown), which is a common phenomenon and is probably due to the transcriptional activity of the region in which the construct was inserted. GUS staining was detectable in seeds after 1d germination and detected strongly in cotyledons 3 d post-germination. As the seedlings grew, GUS staining in cotyledons peaked in days 6–8 post-germination, gradually decreased and became undetectable 2 weeks after germination (Panels A–E, FIG. 5). In comparison, GUS staining in transgenic plants containing rpL34 promoter can be detected in leaf primordia and developing leaves at later stages of growth and development (Panels F–J, FIG. 5). Consistently, the GUS activity measurement for the rpL25 construct during seed germination and seedling growth and development showed similar pattern (FIG. 6). This pattern of rpL25 promoter conferred expression corresponds well with the measured mRNA level (Gao et al. 1994. Plant. Mol. Biol. 25:761–770), suggesting that rpL25-3 contains the full-length promoter. These results indicate that the expression of rpL25 gene is tissue-specific and developmentally regulated, and that rpL25-3 probably has the full function of the promoter region of the rpL25 gene.

We claim:

1. An isolated DNA molecule comprising the nucleotide sequence of SEQ ID NO: 2.

2. An expression vector comprising a promoter comprising the DNA molecule of claim 1 and a structural gene operably linked thereto.

3. A plant cell transformed with the expression vector of claim 2.

4. A plant transformed with the expression vector of claim 3.

5. A seed obtained from the plant of claim 4.

6. A chimeric gene comprising:
   a promoter comprising the isolated DNA molecule of claim 1; and
   a coding nucleotide sequence encoding a gene product other than the *Nicotiana tabacum* L25 gene product, the promoter being operably linked to the coding sequence.

7. The chimeric gene of claim 6 wherein the gene product is an enzyme.

8. The chimeric gene of claim 6 within a host cell.

9. The chimeric gene of claim 8 integrated into the genome of the host cell.

10. An isolated promoter comprising at least nucleotides 805–885 of SEQ ID NO:2.

11. The isolated promoter of claim 10 comprising at least nucleotides 728–885 of SEQ ID NO: 2.

12. A vector comprising the promoter of claim 10.

13. A nucleotide construct comprising the isolated promoter of claim 10 fused in transcriptional controlling relation to a coding sequence encoding a protein of interest.

14. A vector comprising the nucleotide construct of claim 13.

15. A host cell comprising the nucleotide construct of claim 13.

16. The host cell of claim 15 wherein the host cell is comprised by a member of the group consisting of a plant, a plant tissue, and a seed.

17. The host cell of claim 15 wherein the host cell belongs to a plant species other than *Nicotiana tabacum*.

18. The host cell of claim 15 wherein the host cell is a bacterium.

* * * * *

UNITED STATES PATENT AND TRADEMARK OFFICE
CERTIFICATE OF CORRECTION

PATENT NO. : 6,783,978 B1
DATED : August 31, 2004
INVENTOR(S) : Shi et al.

It is certified that error appears in the above-identified patent and that said Letters Patent is hereby corrected as shown below:

<u>Title page,</u>
Item [56], References Cited, OTHER PUBLICATIONS,
"jeeninga et al." reference, replace "jeeninga" with -- Jeeninga --.
"J. Gao et al.," reference, replace "Portein" with -- Protein --.

Delete Drawing Sheet 6 of 6 and substitute therefore the attached Drawing Sheet 6 of 6.

<u>Column 1,</u>
Line 42, replace "primordial" with -- primordia --.
Lines 49-53, delete "ribosomal protein genes in prokaryotes (Mager 1988. Biochim Biophys. Acta 949:1-15). The rpL16 in Arabidopisis is encoded by two genes (rpLA and rpL16B), and both are mainly regulated in the level of transcription (Williams et al. 1995. Plant J. 8:65-76),".

<u>Column 6,</u>
Line 23, replace "37C" with -- 37°C --.

<u>Column 13,</u>
Line 18, replace "3" with -- 2 --.

Signed and Sealed this

Fourth Day of October, 2005

JON W. DUDAS
*Director of the United States Patent and Trademark Office*